US010288596B2

(12) United States Patent
Gammon et al.

(10) Patent No.: US 10,288,596 B2
(45) Date of Patent: May 14, 2019

(54) METHOD OF CALIBRATING A WATER DETECTION UNIT

(71) Applicant: GAMMON TECHNICAL PRODUCTS, INC., Manasquan, NJ (US)

(72) Inventors: James H. Gammon, Manasquan, NJ (US); Michael Leggiero, Manasquan, NJ (US); David Fetzer, Toms River, NJ (US)

(73) Assignee: GAMMON TECHNICAL PRODUCTS, INC., Manasquan, NJ (US)

( * ) Notice: Subject to any disclaimer, the term of this patent is extended or adjusted under 35 U.S.C. 154(b) by 278 days.

(21) Appl. No.: 15/350,337

(22) Filed: Nov. 14, 2016

(65) Prior Publication Data

US 2017/0138854 A1 May 18, 2017

Related U.S. Application Data

(60) Provisional application No. 62/254,857, filed on Nov. 13, 2015.

(51) Int. Cl.
*G01N 33/22* (2006.01)
*G01N 21/77* (2006.01)

(52) U.S. Cl.
CPC .......... *G01N 33/22* (2013.01); *G01N 21/77* (2013.01); *G01N 2021/7786* (2013.01); *G01N 2201/13* (2013.01)

(58) Field of Classification Search
CPC . G01N 33/22; G01N 21/77; G01N 2021/7786

USPC .................................................. 427/157, 158
See application file for complete search history.

(56) References Cited

U.S. PATENT DOCUMENTS

| 4,383,378 A    | * | 5/1983  | Lockwood | .............. F26B 15/12 198/436 |
| 2007/0264420 A1 | * | 11/2007 | Davies   | ...................... B42C 9/00 427/8 |
| 2011/0244592 A1 | * | 10/2011 | Arzhakova | .......... G01N 21/643 436/164 |

OTHER PUBLICATIONS http://www.gammontech.com/mainframe/pdf/b086.pdf; Aqua-Glo Series V Water Detector.
https://www.astm.org/Standards/D3240.htm; Standard Test Method for Undissolved Water in Aviation Turbine Fuels.
http://d-2inc.com/product/jf-wa1-jf-wa1-n/;JF-WA1 & JF-WA1-N Hydro-Light Free Water Detector D3240.

* cited by examiner

*Primary Examiner* — Scott W Dodds
(74) *Attorney, Agent, or Firm* — Shumaker, Loop & Kendrick, LLP; James D. Miller (57) ABSTRACT

A kit and method for manufacturing a reference standard for a water detection unit includes a substrate and a tray configured to receive the substrate therein. A tank is configured to receive at least one of the trays therein, wherein a fluorescent solution comprising water and uranine is provided to the tank via an inlet. The solution rises within the tank to saturate the substrate. The trays are then placed in a rotatable rack wherein the substrates are dried to remove excess solution. The dried substrates are then hermetically sealed within a transparent envelope.

7 Claims, 6 Drawing Sheets

METHOD OF CALIBRATING A WATER DETECTION UNIT

CROSS-REFERENCES TO RELATED APPLICATIONS

The application claims priority to U.S. Provisional Patent Application No. 62/254,857, filed Nov. 13, 2015, the disclosure of which is incorporated herein by reference in its entirety.

FIELD OF THE INVENTION

The invention relates to a method of water detection, and more particularly to a method for calibrating a water detection unit for fuel.

BACKGROUND

Water detection units are commonly employed to detect and measure a presence of undissolved water within a fuel supply. One common use of water detection units is in the aviation industry, for detecting and measuring undissolved water in jet fuel.

One common test for measuring undissolved water in jet fuel involves passing a measured sample of fuel through an absorbent filter pad, wherein an upstream side of the filter pad is coated with a uranine dye. See MIL-DTL-81248, for example. The filter pad is then illuminated using an ultraviolet (UV) light, wherein a presence of undissolved water on the coated side of the pad will cause the pad to fluoresce a bright yellow. The fluorescence of the pad is directly related to an amount of undissolved water present in the pad, wherein a greater amount of undissolved water results in a brighter fluorescence. Using a photocell or similar comparator, the UV-illuminated pad is then directly or indirectly compared to a reference standard having a known emittance, and the amount of undissolved water in the sample is determined.

In order to accurately determine an amount of undissolved water in a fuel sample, the water detection unit must be calibrated prior to use. To calibrate the water detection unit, a filter pad having a known amount of fluorescence, known as a reference standard or calibration standard, is loaded into the detection unit and subjected to UV light. A readout of the water detection unit is then adjusted until an indicated emittance matches a known emittance of the reference standard.

A common method for manufacturing reference standards involves providing a paper filament pad. One side of the paper filament pad is then treated with a fluorescent material. However, reference standards are difficult to manufacture, as substances that will absorb and emit UV light within the same spectrum of visible light are rare. Known organic substances, like unreacted uranine, are unstable and unlikely to provide repeatable and reproducible readouts over a period of time, while inorganic substances tend to not follow the same emittance curves as the test material, uranine.

As testing has evolved from being a simple visual test, to using sophisticated photocells and sensors, the use of inorganic materials having a different emittance curve than uranine has become problematic, as it is more likely to result in inaccurate calibration of the water detection unit. Particularly, older testing units were relatively insensitive to wavelengths of light, wherein dyes having different wavelengths could be used to calibrate the detection unit so long as the emittance was comparable to that of the uranine used on the actual test pad. However, modern detection units are highly sensitive to the wavelength of the emittance. Thus, the emittance of the reference standard must have a wavelength similar to the emittance of the test pads. Accordingly, conventional dyes are no longer reliable in a reference standard, as the wavelengths are different than the uranine used on the test pads.

Additionally, the fluorescents used in many reference standards have a high level of persistence, wherein the emittance of the material continues for an extended period of time after exposure of the fluorescent to UV light. High persistence may have an effect on subsequent readings when taken quickly in series, as residual emittance of the fluorescent may be erroneously included in the subsequent reading.

It is therefore desirable to provide a means of manufacturing a reference standard using a stable material that follows an emittance curve comparable to the emittance curve of uranine.

SUMMARY OF THE INVENTION

In concordance with the instant disclosure, a means of manufacturing a reference standard using a stable material that follows an emittance curve comparable to the emittance curve of uranine is surprisingly discovered.

In one embodiment, a kit for manufacturing a reference standard for a water detection unit is provided. The kit includes an absorbent polymeric substrate. A tray is configured to receive at least one of the substrates therein. A tank is configured to receive the tray therein, and has a fluid inlet for communicating a fluorescent solution from an external fluid source to an interior cavity of the tank. The inlet is disposed in a lower portion of the tank. A rotatable drying rack includes at least one compartment configured to receive the tray therein. The fluorescent solution comprises water and uranine.

In another embodiment, a method of manufacturing the reference standard includes providing a substrate and a fluorescent solution. The fluorescent solution comprises a mixture of water and uranine, wherein the concentration of the uranine ranges from about $6.25 \times 10^{-5}$ percent to about $6.25 \times 10^{-4}$ percent by volume. The substrate is saturated within the solution and then dried to remove excess solution. The substrate is then laminated within a transparent film to hermetically seal the substrate.

In yet another embodiment, a method of manufacturing the reference standard includes securing an absorbent polymeric substrate within a conduit of a tray. The tray is then placed within a tank, and a fluorescent solution is introduced to the tank, wherein the tray is submerged within the solution and the solution is wicked through the substrate to saturate the substrate. The tray is then removed from the tank and dried using a rotatable drying rack. After drying, the substrate is hermetically sealed within a transparent envelope.

DETAILED DESCRIPTION OF THE INVENTION

The following detailed description and appended drawings describe and illustrate various embodiments of the invention. The description and drawings serve to enable one skilled in the art to make and use the invention, and are not intended to limit the scope of the invention in any manner. In respect of the methods disclosed, the steps presented are exemplary in nature, and thus, the order of the steps is not necessary or critical.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components, or process steps, the present technology also specifically includes embodiments comprising, consisting of, or consisting essentially of, such materials, components, or process steps including additional materials, components, or processes (for comprising), excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments comprising, consisting of, and consisting essentially of, A, B and C, excluding an element D that may be recited in the art, even though element D is not explicitly described as being excluded herein.

Referring to FIGS. 1-5C, a kit for producing a reference standard 10 for a water detection unit is provided. The kit includes a substrate 12 for forming the reference standard 10, at least one tray 14, a soaking tank 16, a drying rack 18, and a fluorescent solution 20.

The substrate 12 may be formed of polymeric mesh fabric configured to absorb the solution 20. In one embodiment, the substrate 12 may be provided as an absorbent cylindrical pad formed of a polymeric material, such as a polyethylene terephthalate (PET), commonly sold under the trade name Dacron®. For example, membranes such as EMD Millipore part number AAWP037P0, which are 37 millimeters in diameter and 150 micrometers thick, have been found to offer favorable results. In alternate embodiments, the substrate 12 may be provided as a sheet, wherein the sheet is cut into individual pads after treatment with the fluorescent solution 20, as discussed below. Those of ordinary skill in the art will appreciate other materials, shapes, and thicknesses of substrates 12 suitable for use in producing reference standards 10.

Figure 1:
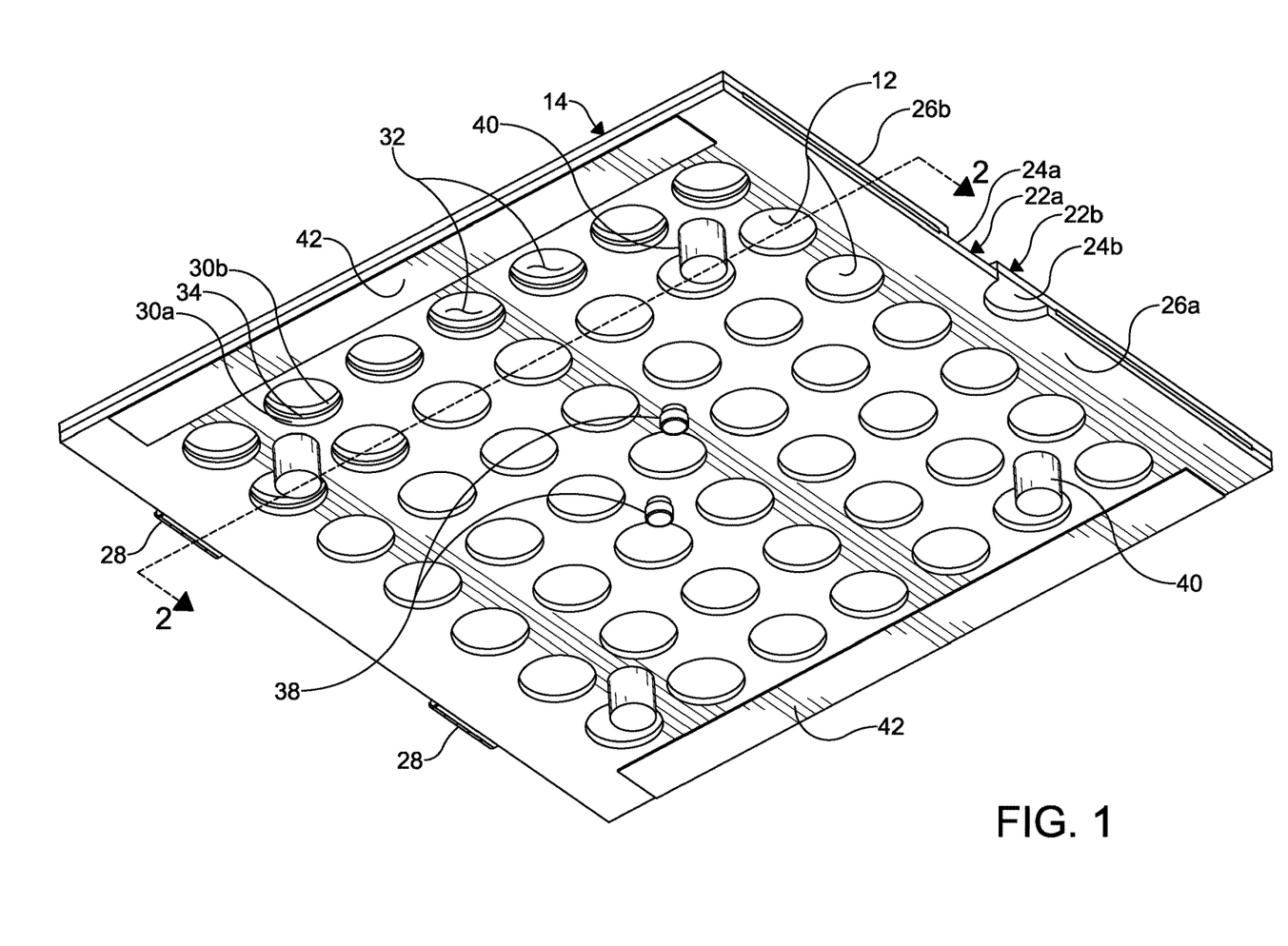
FIG. 1 is a bottom perspective view of a tray of a kit for producing a reference standard according to the instant disclosure.
Figure 2:
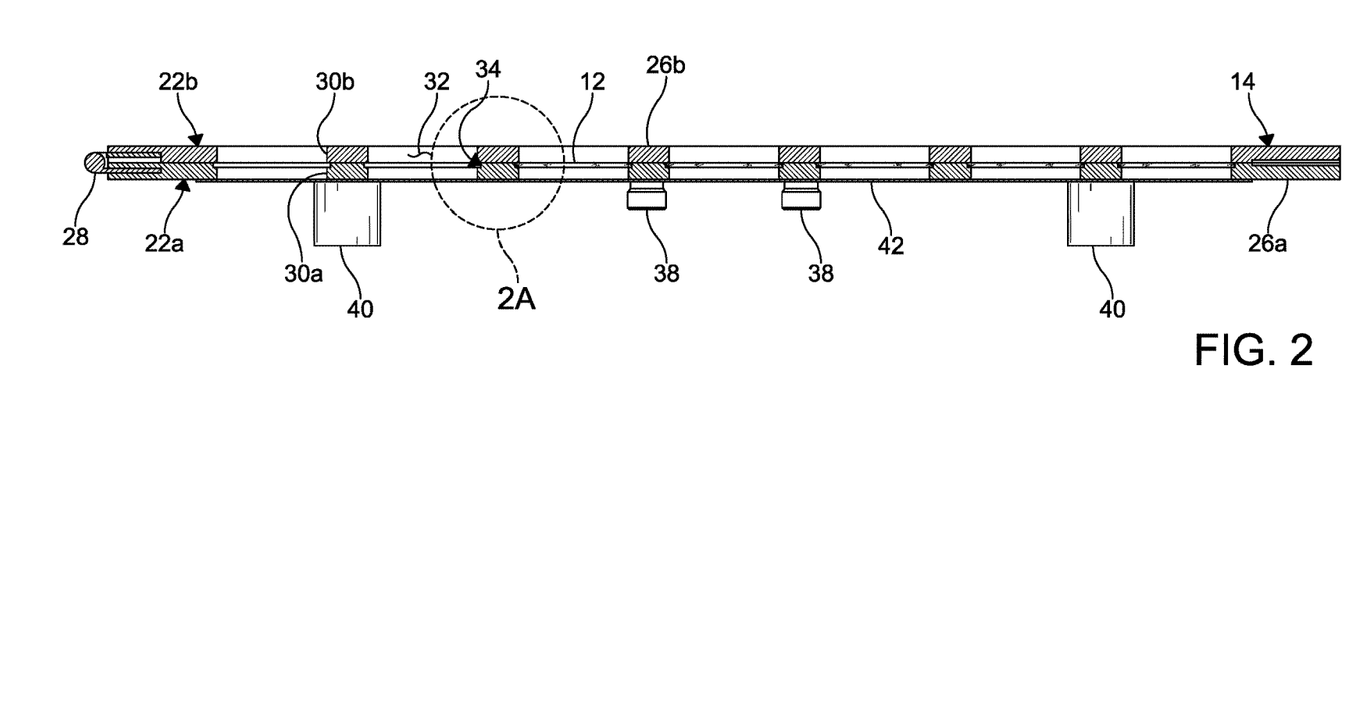
FIG. 2 is a cross-sectional view of the tray of FIG. 1, taken through section line 2-2 of FIG. 1.
Figure 2A:
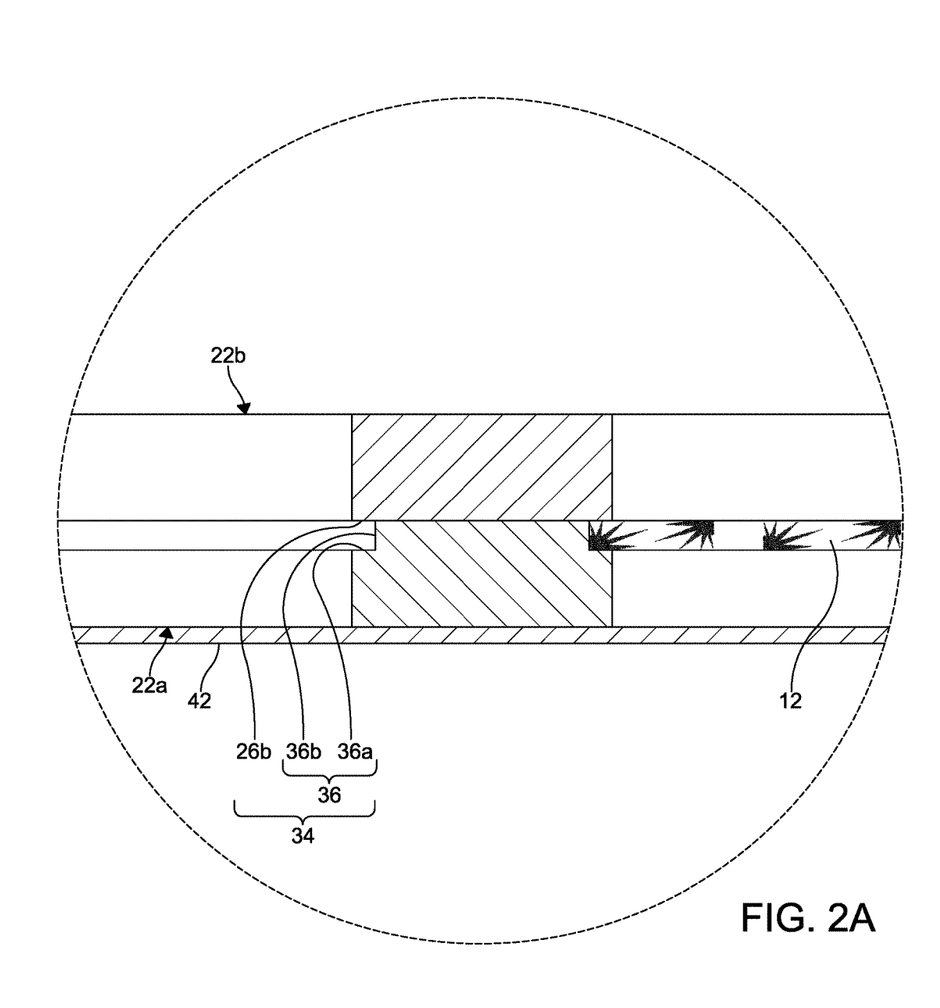
FIG. 2A is an enlarged cross-sectional view of the tray of FIG. 1, taken at area 2A of FIG. 2.

As shown in FIGS. 1-2A, the tray 14 includes a first bottom plate 22a and a second top plate 22b each having an inner face 24a, 24b and an outer face 26a, 26b. The tray 14 is configurable in an open position and a closed position. In the closed position, shown in FIGS. 1-2A, the respective inner faces 24a, 24b of the bottom plate 22a and the top plate 22b abut each other in a face-to-face arrangement. In the open position (not shown), the inner faces 24a, 24b of the plates 22a, 22b are spaced apart from each other, wherein the inner faces 24a, 24b of the plates 22a, 22b are easily accessible. In the illustrated embodiment the tray 14 includes at least one hinge 28 configured to rotatably couple the bottom plate 22a and the top plate 22b to each other. However, in alternate embodiments the plates 22a, 22b may be independent from each other, wherein the top plate 22b is removed from the bottom plate 22a when the tray 14 is in the open position. Further, the tray 14 is non-buoyant in the solution 20, wherein the tray 14 will remain stationary within the tank 16 when the tray 14 is submerged within the solution 20.

A plurality of apertures 30a, 30b are formed through each of the bottom plate 22a and the top plate 22b, wherein the apertures 30a of the bottom plate 22a correspond with the apertures 30b of the top plate 22b to form a plurality of conduits 32 when the tray 14 is in the closed position. Each one of the conduits 32 is configured to retain one of the substrates 12 therein, wherein the solution 20 can pass through the substrate 12 via the conduit 32. As shown, the apertures 30a, 30b are cylindrical in shape to correspond to the cylindrical substrate 12. In alternate embodiments the apertures 30a, 30b may have a polygonal or irregular cross section to correspond to a polygonal or irregularly shaped substrate 12, respectively.

A retaining groove 34 is formed in a sidewall of each of the conduits 32, and is configured to receive an outer perimeter of the substrate 12 therein. In the illustrated embodiment, the retaining groove 34 is formed intermediate the bottom plate 22a and the top plate 22b, and is configured to secure the substrate 12 between the bottom plate 22a and the top plate 22b when the tray 14 is in the closed position. In alternate embodiments, the recess 36 may be formed entirely in the top plate 22b, or partially in each of the top plate 22b and the bottom plate 22a.

Referring to FIG. 2A, the retaining groove 34 is defined by a recess 36 formed in the inner face 24a of the bottom plate 22a, wherein the recess 36 circumscribes a perimeter of the aperture 30a in the bottom plate 22a. The recess is defined by an outer sidewall 36a offset outwardly from the sidewalls of the conduit 32, and a planar ledge 36b. A size of the groove is configured to maximize exposure of the substrate 12 within the conduit 32, while securely retaining the substrate 12 within the conduit 32. For example, a width of the groove 34, which is a distance from the ledge 36b to the inner face 24b of the top plate 22b, may be equal to or greater than the thickness of the substrate 12, wherein the substrate 12 is retained within the groove 34 when the tray 14 is in the closed position. Particularly, the substrate 12 should fit securely within the groove 34, wherein only a minimal clearance exists between the substrate 12 and the groove 34 to prevent compression of the substrate 12. Similarly, a depth of the retaining groove 34, which is a distance from the sidewall of the conduit 32 to the outer sidewall 36a of the recess 36, provides a minimal offset from the sidewalls of the conduit 32.

The tray 14 further includes a coupling means 38 and a support means 40 formed thereon. The coupling means 38 is configured to secure the tray 14 in the closed position when the inner faces 24a, 24b of the plates 22a, 22b are abutted. In the illustrated embodiment, the coupling means 38 is a threaded fastener, wherein the fastener extends through a first one of the plates 22a, 22b to engage threads formed in the other one of the plates 22a, 22b. However, the coupling means 38 may be also be a clamping device, a magnetic device, or another type of securing means configured to secure the tray 14 in the closed position.

Figure 3:
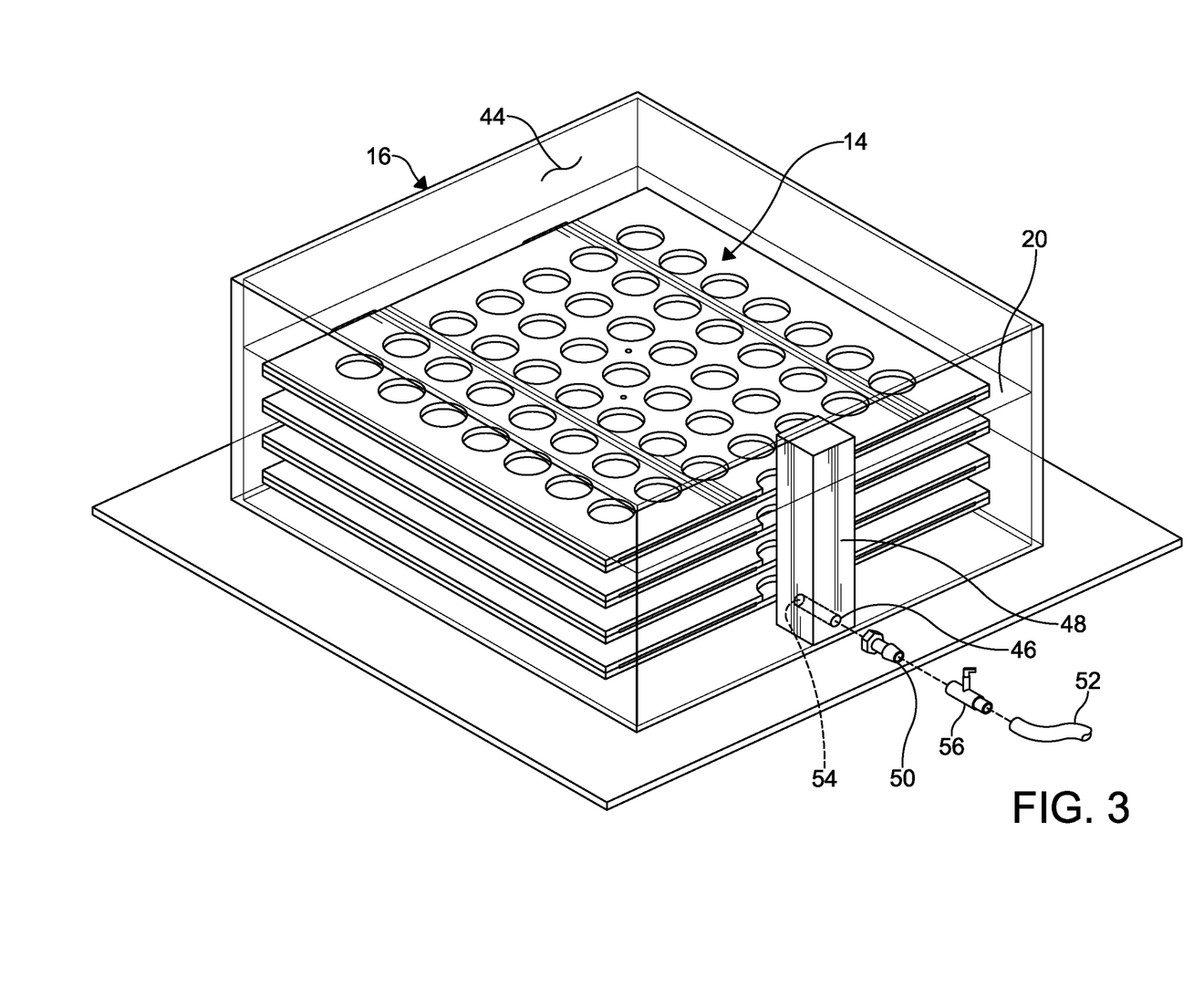
FIG. 3 is a top perspective view of a tank of the kit for producing the reference standard according to the instant disclosure; wherein a plurality of the trays of FIG. 1 are received in the tank.

The support means 40 is configured to provide a space between the tray 14 and an adjacent surface when the tray 14 is set atop the adjacent surface. For example, the support means 40 may provide a space between the bottom plate 22a of a first tray 14 and the top plate 22b of a second tray 14 when the first tray 14 is stacked atop the second tray 14, as shown in FIG. 3. In the illustrated embodiment, the support means 40 includes a plurality protuberances extending from the outer face 26a of the bottom plate 22a. When a plurality of the trays 14 are stacked, a distal end of the support means 40 of a first tray 14 abuts the outer face 26b of the top plate 22b of a second one of the trays 14, thereby creating a space between the bottom plate 22a of the first tray 14 and the top plate 22b of the second tray 14.

The tray 14 may also include at least one magnetic strip 42 formed along the outer face 26a of the bottom plate 22a, wherein the magnetic strip 42 is configured to magnetically couple the tray 14 within the drying rack 18, as further described below.

The soaking tank 16 includes an interior cavity 44 configured to receive at least one of the trays 14 therein. In the illustrated embodiment, the soaking tank 16 is a box-shaped structure configured to receive a plurality of the trays 14, as shown in FIG. 3. The soaking tank 16 includes an inlet 46 configured to provide fluid communication between an external fluid source (not shown) and the interior cavity 44 of the soaking tank 16. In the illustrated embodiment, the inlet 46 is formed in a manifold block 48 disposed in the interior cavity 44, the manifold block 48 having a threaded receptacle for receiving a hose connection 50 disposed on an exterior of the soaking tank 16. The hose connection 50 is configured to be fluidly coupled with a hose 52 from the external fluid source. An outlet 54 provides fluid communication from the inlet 46 to the interior cavity 44 of the soaking tank 16, and is disposed beneath the trays 14, wherein the solution 20 is fed to the interior cavity 44 from a lower portion of the tank 16. By providing the solution 20 from the lower portion of the tank 16, each of the stacked trays 14 is uniformly submerged as the solution 20 rises. In contrast, feeding the soaking tank 16 from a position above the trays 14 may cause uneven distribution of the solution 20 across the trays 14 as the interior cavity 44 is filled. The inlet 46 may include an adjustable valve 56, wherein a flow rate of the solution 20 into the interior cavity 44 of the tank 16 can be adjusted. Although the illustrated embodiment of the soaking tank 16 is passively supplied via a gravity feed, the soaking tank 16 may optionally be actively supplied by a pumping means configured to meter the solution 20 into the tank 16 at a controlled flow rate.

Figure 4:
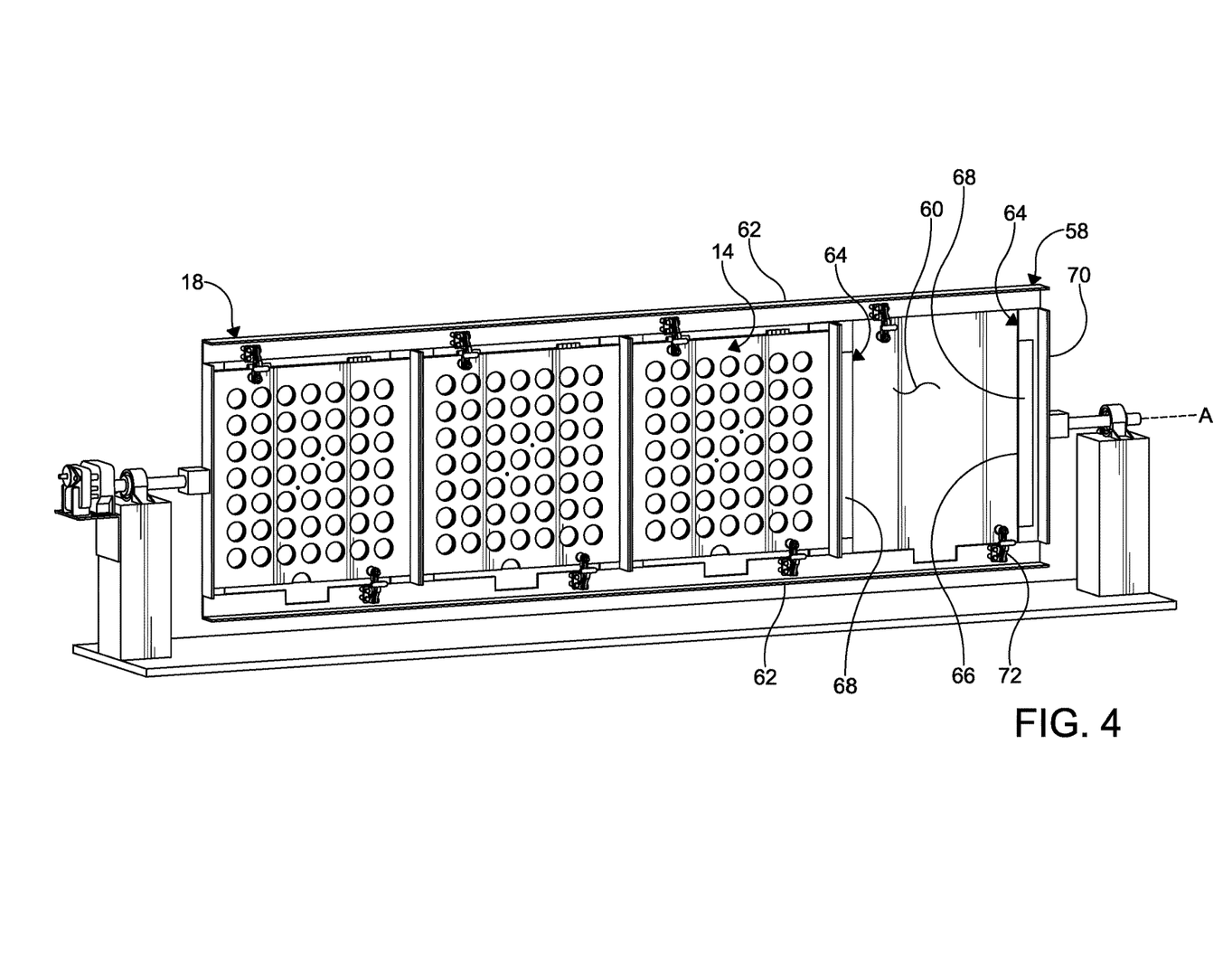
FIG. 4 is a front perspective view of a drying rack of the kit for producing the reference standard according to the instant disclosure, wherein a plurality of the trays of FIG. 1 are received in the drying rack.
Figure 5A:
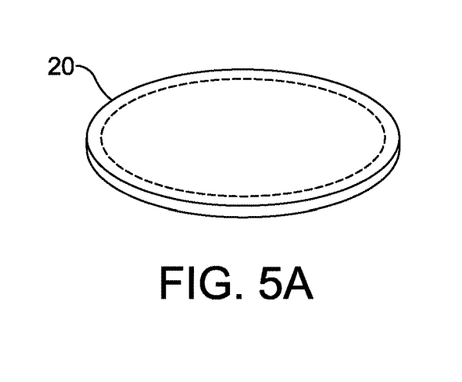
FIG. 5A is a top perspective view of a substrate for making a reference standard according to the instant disclosure.
Figure 5B:
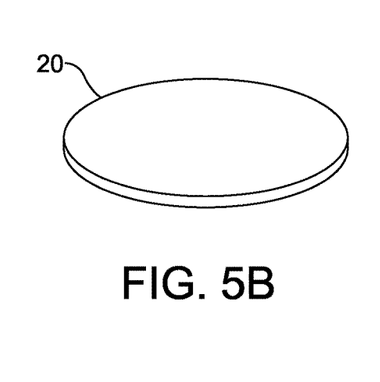
FIG. 5B is a top perspective view of the substrate of FIG. 5A, wherein an outer perimeter of the substrate has been removed.
Figure 5C:
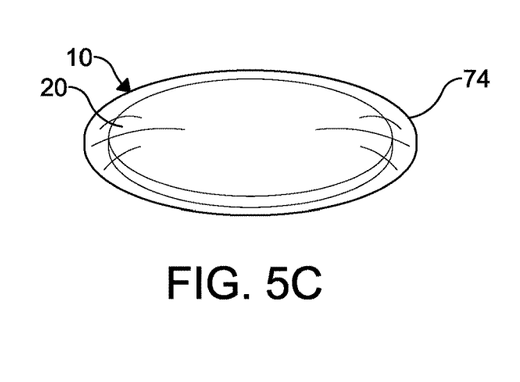
FIG. 5C is a top perspective view of a reference standard according to the instant disclosure.

The drying rack 18 includes a rotatable frame 58 assembly having a plurality of compartments 60, wherein each of the compartments 60 is configured to secure one of the trays 14 to the frame 58 assembly. The illustrated frame 58 assembly is formed of a pair of opposing longitudinal sides 62 connected to each other by a plurality of longitudinally spaced crossmembers 64, wherein opposing ones of the crossmembers 64 cooperate with the sides 62 to define each of the compartments 60. Accordingly, the compartments 60 of the illustrated embodiment are consecutively arranged in a single row along a rotational axis A of the frame 58. However, in alternate embodiments, the compartments 60 may be arranged in a plurality of rows, for example.

The crossmembers 64 each include a planar base 66 for receiving a portion of the tray 14 thereon. As shown the base 66 may have a magnetic strip 68 disposed thereon, wherein the magnetic strips 68 of the crossmembers 64 are configured to cooperate with the magnetic strips 42 of the tray 14 to magnetically secure the tray 14 to the frame 58. The crossmembers 64 of the illustrated embodiment are separately formed L-shaped channels, and further include an upper sidewall 70 extending perpendicularly from the base 66, wherein the sidewall of a first one of the crossmembers 64 cooperates with the sidewall of an adjacent one of the crossmembers 64 to form a divider between adjacent ones of the compartments 60. In alternate embodiments, the crossmembers 64 may be substantially planar, wherein a single crossmember 64 is configured to support two of the adjacent trays 14.

Each compartment 60 of the frame 58 may further include at least one clamping device 72 for securing each tray 14 therein. In the illustrated embodiment, the clamping device 72 is a toggle clamp.

The kit further comprises a transparent envelope 74 configured to receive the substrate 12 therein. In one embodiment, the envelope 74 is formed of a transparent film. It has been discovered that a transparent film having a matte, or non-glare surface beneficially provides a diffusive effect, and provides more uniform readings when the reference standard 10 is used within water detection unit. For example, Jackson-Hirsch part number 9X11-6NG2 has been discovered to perform favorably.

The kit may include a hydraulic press (not show) configured to apply a pressure between 2,000 pounds per square inch and 10,000 pounds per square inch. A conventional drying oven (not shown) capable of receiving at least one of the trays 14 therein may also be provided.

In another embodiment of the disclosure a method for producing the reference standard 10 is provided. Initially, the fluorescent solution 20 is prepared. The solution comprises a mixture of water and a fluorescent element. The water may be any one of a spring water, a distilled water, a filtered water, a bottled water, a tap water, a deionized water or a combination thereof, for example. The fluorescent element of the solution may be fluorescein disodium salt, commonly known as uranine, which is identified as CAS Number 518-47-8.

A concentration of the uranine in the solution 20 is configured to provide a predetermined emittance when the solution 20 is applied to the substrate 12 and subjected to an ultraviolet light, as discussed further below. In the illustrative embodiment, the uranine is provided in a percentage of the total volume of the solution 20 in a range of about $6.25 \times 10^{-5}$ percent to about $6.25 \times 10^{-4}$ percent. By mixing the uranine and the water in the prescribed proportions, the uranine reacts with the water, producing a predetermined fluorescence. Different concentrations of uranine may be selected depending on the desired emittance of the pad. Reference standards having different levels of emittance are then used to calibrate a detection unit, as described below.

In another step of the method, the substrate 12 is prepared for treatment with the solution 20. The illustrated substrate 12 is initially provided with a substantially smooth first side and a textured second side. However, it has been surprisingly discovered that the textural differences between the first side and the second side causes saturation of the substrate 12 to be non-homogenous, resulting in inconsistent readings when the substrate 12 is used as a reference standard. Accordingly, to provide a uniform texture on both sides of the substrate 12, the substrate 12 is compressed in a prepressing step. For example, a pressure between 1,000 pounds per square inch and 10,000 pounds per square inch is applied to the substrate 12 to flatten the textured second side, and more preferably, a pressure of about 2,400 pounds per square inch is applied in the prepressing step.

After the prepressing step, the substrate 12 is then subjected to a solution 20 application step, wherein the substrate 12 is saturated with the fluorescent solution 20. In one embodiment of the method, the substrate 12 is secured within one of the conduits 32 of the tray 14, and the tray 14 is placed within the tank 16. The solution 20 is provided to interior cavity 44 of the tank 16 via the inlet 46 until the substrate 12 is completely submerged within the solution 20. In the illustrative embodiment, the solution 20 is provided to the tank 16 via a metered flow, wherein the flow rate of the solution 20 into the tank 16 is minimized. Particularly, the solution 20 is provided at a rate wherein no pressure is applied to the substrate 12 by the solution 20, and the solution 20 is allowed to absorb into the substrate 12. Providing the solution 20 to the tank 16 from the inlet 46 beneath the substrate 12 at a minimized flow rate has been discovered to improve the homogeneity of the saturation of the substrates 12.

The substrate 12 is then left to soak in the solution 20 to ensure complete and uniform saturation of the substrate 12 with the solution 20. It has been discovered that five minutes is sufficient to ensure saturation of the substrate 12.

In other embodiments, the uranine solution 20 may be applied to the pad by spraying, or may be provided to the tank 16 from a position above the substrate 12. Other methods of saturating the substrate 12 with the solution 20 will be appreciated by those of ordinary skill in the art.

The substrate 12 is then removed from the tank 16 for a drying step. In one embodiment, the solution 20 is drained from the tank 16 prior to removal of the trays 14. A flow rate of the solution 20 from the tank 16 is minimized similar to the flow rate of the solution 20 into the tank 16, as described above. Accordingly, during draining of the solution 20 from the tank, minimal pressure is exerted on the substrate 12 by the solution 20. In alternate embodiments, the trays 14 may be removed from the tank 16 prior to draining the solution 20 therefrom.

The substrate 12 may remain in the tray 14 during the drying step. Initially, each of the trays 14 may be shaken to remove any excess solution 20 that may remain on the tray 14. The tray 14 is then provided to the compartment 60 of the drying rack 18, wherein the magnetic strips 42 of the tray 14 are magnetically coupled to the magnetic strips 68 of the frame 58, and the tray 14 is secured using the coupling means 38. The drying rack 18 is then rotated for a period of time until excess solution 20 has evaporated from the substrate 12. A speed of the rotation is minimized, wherein centrifugal force applied to the solution 20 and the substrates 12 is negligible, and the force of gravity beneficially serves to homogenously distribute the solution 20 throughout the substrate 12 as the substrate 12 dries. Generally the substrate 12 will be dried to the point where no solution 20 runs freely within the substrate 12 or can be blotted from the substrate 12. The substrate 12 may finally be dried using a heating step, either during or after the rotational drying step. During the heating step, the substrate 12 is subjected to an elevated temperature to accelerate evaporation of the solution 20. For example, the pad may be subjected to a temperature between about 100 and 200 degrees Fahrenheit, and preferably about 125 degrees Fahrenheit, wherein the trays are safe to handle by hand. However, other temperatures may be used to accelerate or decelerate drying during the heating step. After heated drying, the pad will be dry to the touch.

The dried substrate 12 is then trimmed to remove the outer perimeter of the substrate 12 as indicated by the dashed line in FIG. 1A. In the illustrated embodiment, the cylindrical pad is trimmed from the initial 37 millimeter diameter to approximately 19 millimeters. By trimming the substrate 12 after saturation and drying, a nonhomogeneous "halo" formed on the perimeter, caused by the perimeter of the substrate 12 being contained within the retaining groove 34 during saturation, is removed from the substrate 12 to ensure uniformity.

After trimming, the substrate 12 is pressed a second time to ensure uniformity of the first side and the second side of the substrate 12, as it has been discovered that during saturation and drying residual stresses in the fibers of the substrate 12 cause the textured surface of the second side of the substrate 12 to return. In the second pressing step, a pressure of between about 4,000 pounds per square inch and about 10,000 pounds per square inch, and more preferably, about 9,100 pounds per square inch, is applied to the substrate 12. It has been discovered that increased pressures provide more favorable results.

The trimmed substrate 12 is then hermetically sealed within the transparent envelope. In the illustrated embodiment, envelope is formed of a transparent film, which is applied to the substrate 12 using a lamination process, as is known in the art. The envelope is then trimmed to fit within the water detection unit. For example, an outer diameter of the envelope may be between 22 millimeters and 25 millimeters, and more preferably, 23 millimeters.

In use, at least one of the reference standards 10 is used to calibrate the water detection unit prior to testing. For example, in older analog detection units, a first reference standard 10 may be permanently installed within the detection unit, while a second reference standard 10 having an emittance comparable to the first reference standard, and referred to as a calibrating pad, may be removably received within detection unit. Prior to each use, the calibrating pad is installed in the detection unit, wherein the measured emittance of the calibrating pad is compared to the measured emittance of the first reference standard to effectively "zero out" the detection unit. In digital water detection units, a plurality of the reference standards 10 having different emittances may be used to construct a calibration curve for the detection unit when the detection unit is assembled. Additionally, the digital detection unit may include a reference standard permanently installed therein, referred to as a compensation pad, which is configured to allow the detection unit to automatically compensate for variances in atmospheric conditions, prior to each test. Those of ordinary skill in the art will appreciate that the illustrated embodiment of manufacturing a reference standard is applicable to calibrating all types of detection units configured to measure a presence of water using a uranine-coated pad.

By manufacturing a reference standard 10 according to the instant disclosure, the emittance of the reference standard 10 follows the same emittance curve as the test pads. Additionally, uranine has been shown to have a relatively low level of persistence compared to other fluorescents used in the art, thereby allowing a reference standard according to the instant disclosure to be used in subsequent calibrations, with a relatively short period of time in between readings.

From the foregoing description, one ordinarily skilled in the art can easily ascertain the essential characteristics of this invention and, without departing from the spirit and scope thereof, can make various changes and modifications to the invention to adapt it to various usages and conditions.

What is claimed is:

1. A method of producing a reference standard, comprising the steps of providing an absorbent substrate;
securing the substrate within a tray;
placing the tray within a tank;
introducing a fluorescent solution into the tank, wherein the substrate is submerged within the solution and the substrate absorbs a portion of the solution;
removing the substrate from the solution, and drying the substrate; and
sealing the substrate within a transparent envelope.

2. The method of claim 1, further comprising a first pressing step before the substrate is submerged, and a second pressing step after the substrate is dried, wherein in each of the pressing steps the substrate is compressed under a pressure of between about 2000 pounds per square inch and about 10,000 pounds per square inch.

3. The method of claim 1, wherein the solution is introduced into the tank from beneath the substrate, and a flow rate of the solution into the tank is minimized.

4. The method of claim 1, wherein the absorbent substrate is first provided as a cylindrical disc having a first diameter, and an outer perimeter of the substrate is removed prior to sealing the substrate within the envelope.

5. The method of claim 1, wherein the fluorescent solution comprises water and uranine.

6. The method of claim 5, wherein a concentration of the uranine ranges from about $6.25 \times 10^{-5}$ percent to about $6.25 \times 10^{-4}$ percent by volume.

7. The method of claim 1, wherein the substrate is formed of polyethylene terephthalate.

* * * * *